United States Patent
Cummings et al.

(10) Patent No.: US 9,772,337 B2
(45) Date of Patent: Sep. 26, 2017

(54) COMPOSITIONS AND METHODS FOR FUNCTIONAL GYLCOMICS

(75) Inventors: Richard D. Cummings, Atlanta, GA (US); David F. Smith, Atlanta, GA (US); Xuezheng Song, Decatur, GA (US)

(73) Assignee: Emory University, Atlanta, GA (US)

( * ) Notice: Subject to any disclaimer, the term of this patent is extended or adjusted under 35 U.S.C. 154(b) by 1100 days.

(21) Appl. No.: 13/885,916

(22) PCT Filed: Nov. 22, 2011

(86) PCT No.: PCT/US2011/061765
§ 371 (c)(1),
(2), (4) Date: Aug. 12, 2013

(87) PCT Pub. No.: WO2012/071371
PCT Pub. Date: May 31, 2012

(65) Prior Publication Data
US 2013/0331280 A1    Dec. 12, 2013

Related U.S. Application Data

(60) Provisional application No. 61/416,331, filed on Nov. 23, 2010, provisional application No. 61/488,356, filed on May 20, 2011.

(51) Int. Cl.
*G01N 33/92*    (2006.01)
*C07C 237/34*   (2006.01)
*C07H 15/18*    (2006.01)
*C40B 40/12*    (2006.01)

(52) U.S. Cl.
CPC ........... *G01N 33/92* (2013.01); *C07C 237/34* (2013.01); *C07H 15/18* (2013.01); *C40B 40/12* (2013.01); *C07B 2200/11* (2013.01)

(58) Field of Classification Search
None
See application file for complete search history.

(56) References Cited

PUBLICATIONS

Gege et al (2008 Carbohydrate Research 343:2361-8).*
Li et al. "Mass spectrometry of fluorocarbon-labeled glycosphingolipids" J. Mass. Spectrom., 2010; 45: 504-519.
Luyai et al. "Facile Preparation of Fluorescent Neoglycoproteins Using p-Nitrophenyl Anthranilate as a Heterobifunctional Linker" Bioconjugate Chem., 2009; 20: 1618-1624.
Ohara et al. "Two-dimensional mapping by high-performance liquid chromatography of pyridylamino oligosaccharides from various glycosphingolipids" Journal of Chromatography, 1991; 586: 35-41.
Park et al. "Fluorescent Glycan Derivatives: Their Use for Natural Glycan Microarrays" ACS Chemical Biology, 2009; 4(9): 699-701.
Song et al. "Fluorescent Glycosylamides Produced by Microscale Derivatization of Free Glycans for Natural Glycan Microarrays" ACS Chemical Biology; 2009; 4(9): 741-750.
Song et al. "Generation of a natural glycan microarray using 9-fluorenylmethyl chloroformate (FmocCl) as a cleavable fluorescent tag" Analytical Biochemistry, 2009; 395: 151-160.
Song et al. "Shotgun glycomics: a microarray strategy for functional glycomics" Nature Methods, 2011; 8: 85-90.
Stine et al. "Comparison of Glycosphingolipids and Antibodies as Receptor Molecules for Ricin Detection" Anal. Chem., 2005; 77: 2882-2888.
Wing et al. "High-performance liquid chromatography analysis of ganglioside carbohydrates at the picomole level after ceramide glycanase digestion and fluorescent labeling with 2-aminobenzamide" Anal Biochem., 2001, 298(2): 207-217.
Extended European Search Report issued for EP Application No. 11843357.2 dated Feb. 26, 2014.

* cited by examiner

*Primary Examiner* — Christopher M Gross
(74) *Attorney, Agent, or Firm* — Emory Patent Group

(57) ABSTRACT

The disclosure relates to labeling glycans and glycosphingolipids from undefined mixtures with chemical moieties that emit light when exposed to electromagnetic radiation and uses of these labeled glycans and glycosphingolipids in microarrays for research and diagnostic purposes. In certain embodiments, the disclosure relates to derivatizing glycosphingolipids with a marker.

7 Claims, 14 Drawing Sheets

COMPOSITIONS AND METHODS FOR FUNCTIONAL GYLCOMICS

CROSS-REFERENCE TO RELATED APPLICATIONS

Figure 1:
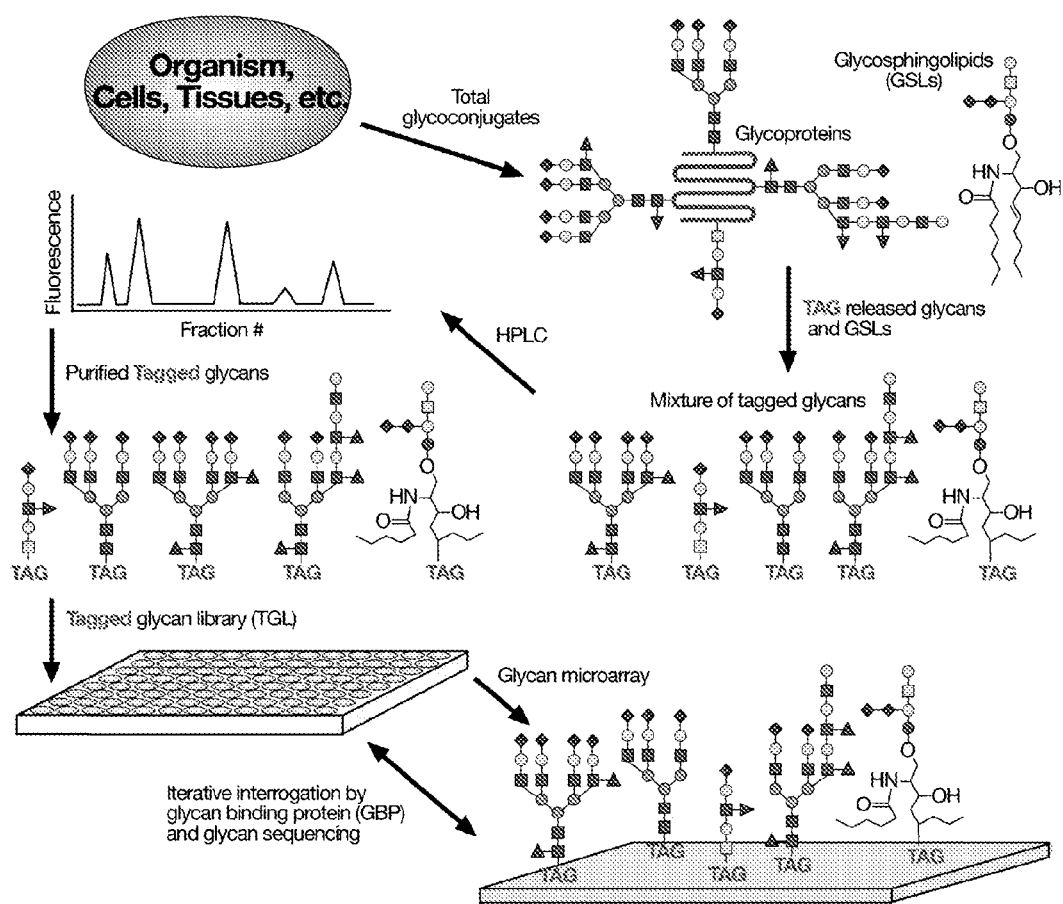

This application claims priority to U.S. Provisional Application No. 61/416,331 filed Nov. 23, 2010, and U.S. Provisional Application No. 61/488,356 filed May 20, 2011 both hereby incorporated by reference in their entirety.

BACKGROUND

The oligosaccharides (glycans) conjugated to proteins and cellular wall components play important roles in cellular signaling and biological activity. For example, the detailed knowledge of the oligosaccharides of recombinantly produced human glycoprotein therapeutics is a prerequisite for their use in patients. From the regulatory point of view (EMEA, FDA), the carbohydrates of therapeutic glycoproteins (e.g. EPO, IFN-β, therapeutic antibodies) play a key role in efficacy and safety (e.g. immunogenicity).

On cellular surfaces, glycans are typically conjugated to proteins (glycoproteins) and ceramides (glycosphingolipids) which are also incorporated into the lipid bilayer. Glycoproteins are also in cellular secretions. Despite progress in high performance liquid chromatography (HPLC), lectin affinity chromatography, mass spectrometry (MS), and glycan microarrays, chemically defining a glycome, the complete list of glycan structures that occur in a cell, tissue, or organism, has been elusive. Studying glycosphingolipids (GSLs) has been especially challenging. In previous approaches to overcome the poor detection sensitivity during HPLC separation of GSLs, the component glycans were released from lipids and analyzed as fluorescent glycans by HPLC. See Wing et al., Anal Biochem, 2001, 298, 207-17 and Ohara et al., J Chromatogr, 1991, 586, 35-41. However, these methods provided no capability to explore GSLs recognition by glycan-binding proteins (GBPs). Thus, there is a need to identify improved methods for detecting and analyzing glycosphingolipids.

There have been a number of methods developed for glycan conjugation. See e.g., Luyai et al., Bioconjugate Chem, 2009, 20 (8), 1618-1624; Song et al., Chem Biol, 2009, 4(9), 741-750; and Song et al., Chem Biol, 2009, 16, 36-47.

SUMMARY

The disclosure relates to labeling glycans and glycosphingolipids with tags, e.g., chemical moieties that fluoresce when exposed to certain wavelengths of light and uses of these tagged glycans and glycosphingolipids in microarrays for research and diagnostic purposes. In certain embodiments, the disclosure relates to derivatizing glycosphingolipids with a fluorescent marker.

In certain embodiments, the disclosure relates to compositions and methods for determining binding of undefined or unknown mixtures of free glycans or glycosphingolipids that are fluorescently tagged, separated by chromatographic means, and printed on microarrays for interrogation with entities that bind to glycan components. Typically, once a positive binding event is identified to a particular undefined or unknown glycan or glycosphingolipid on the microarray, that glycan or glycosphingolipid is then sequenced after recovery from the tagged glycan library. Thus, without a starting knowledge about the structure of a glycan in a mixture, the functionally important glycan in the mixture can be identified by its binding to an entity.

In certain embodiments, the disclosure relates to tagged glycosphingolipids conjugated to a solid surface e.g., glass slide, a bead, polymer, metal, or silicon wafer. The tag that is linked to the glycans and glycosphingolipids is typically a fluorescent molecule, e.g., an aromatic molecule. The tagged glycosphingolipid is typically conjugated through the sphingolipid. A typical tagged glycosphingolipid is one of formula II,

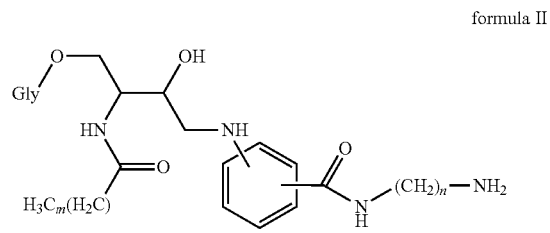

formula II or salts thereof, wherein n is 2, 4, or greater than 4, 8 or greater than 8, m is greater than 4, 9, 12, or greater than 13, and Gly is a glycan. It is contemplated that the hydrocarbon, $(CH_2)_n$ may be replaced with any linker, e.g., polyethylene glycol with a terminal amine group. It is also contemplated that the phenyl moiety may be replaced with any fluorescent molecule or other aromatic molecule, e.g., naphthalene, fluorene. In certain embodiments, it is contemplated that the terminal amine may be replaced with other molecular entities that can be used for conjugation to a solid surface, e.g., the terminal amine may be replaced with or conjugated to biotin or an antibody epitope and further linked to a surface with avidin, streptavidin, or a corresponding antibody.

In certain embodiments, the disclosure relates to a solid surface comprising a plurality of zones wherein the zones comprise purified tagged glycosphingolipids or purified tagged glycans conjugated to the surface provided that at least one of the zones comprises tagged glycosphingolipids.

In certain embodiments, the disclosure relates to methods for determining binding of an entity to a glycan or glycosphingolipid comprising a) conjugating mixtures of glycans and glycosphingolipids with fluorescent tags providing tagged glycans and tagged glycosphingolipids, b) separating the tagged glycans and tagged glycosphingolipids by chromatography providing purified tagged glycans and purified tagged glycosphingolipids, and c) arranging purified tagged glycans and purified tagged glycosphingolipids in an array configured for interrogation with entities that bind to glycan components.

In certain embodiments, the method further comprises the step of identifying a positive binding event is to a specific purified tagged glycan or purified tagged glycosphingolipid on the array through florescent changes in the tagged glycan or tagged glycosphingolipid when mixed with a glycan binding entity. In certain embodiments, the method further comprises the step of sequencing the specific glycan or glycosphingolipid. In certain embodiments, the method further comprises the step of recording that the entity binds to the specific glycan or glycosphingolipid sequence. Typically the data is recorded on a computer. In certain embodiments, the method further comprises the step of reporting entity binding to a subject or medical professional.

In certain embodiments, the disclosure relates to methods of producing a glycan library comprising: a) conjugating a tag to glycosphingolipids and conjugating a tag to glycans released from glycoproteins or other macromolecules containing covalently bound glycans providing a mixture of tagged glycosphingolipids and tagged glycans; b) purifying the tagged glycosphingolipids and purifying the tagged glycans; c) conjugating the purified tagged glycosphingolipids to a solid surface; and d) conjugating the purified tagged glycans to a solid surface.

In certain embodiments, the disclosure relates to methods comprising: a) mixing glycosphingolipids with an oxidizing agent under conditions such that an oxidized sphingosine moiety is formed; and b) linking a marker to the oxidizing sphingosine moiety providing tagged glycosphingolipids wherein the marker comprises an aromatic group. Typically, the oxidizing agent is ozone. Typically, the aromatic group is a phenyl group. In some embodiments, the marker comprises a strait chain hydrocarbon with a terminal amine group.

In certain embodiments, the marker comprises a chemical moiety of formula I:

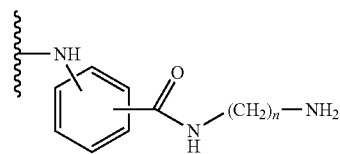

Formula I or salts thereof wherein n is 2, 4, or greater than 4. In a typical embodiment, n is 8 or greater. In certain embodiments, the method further comprises the step of moving the tagged glycosphingolipids through a separation medium providing isolated fractions of tagged glycosphingolipids Typically, the separation medium is a normal phase and/or reverse phase high pressure liquid chromatography column.

In certain embodiments, the method further comprises the step of analyzing an isolated fraction for molecular structure. Typically, analyzing the isolated fraction for molecular structure is determining the molecular weight of the molecule structure or components of the molecular structure using mass spectrometry and correlating the found weight to chemical components with a calculated weight in combination with evaluation with known glycan binding entities.

In certain embodiments, the method further comprises the step of arranging the separated tagged glycosphingolipids on a solid support/substrate into a plurality of zones and determining the affinity of an antibody for an epitope or protein with affinity for a specific glycan or other chemical moiety in the isolated fractions.

In certain embodiments, the disclosure relates to methods of determining an aberrant phenotype of a subject comprising, a) linking markers to glycans with and without sphingolipids in a sample wherein the markers comprises an aromatic group providing tagged glycans and glycosphingolipids; moving the tagged glycans and glycosphingolipids through a separation medium providing isolated fractions; arranging isolated fractions into a plurality of zones; and analyzing the zones for an indication of a normal or aberrant phenotype.

In certain embodiments, analyzing the zones for an indication of a normal or aberrant phenotype comprises the steps of e) identifying a pattern within the markers; f) comparing the pattern with a pattern obtained from a normal phenotype; and g) correlating a similar pattern to a normal phenotype.

In certain embodiments, analyzing the zones for an indication of a normal or aberrant phenotype comprises the steps of e) identifying a pattern within the markers; f) comparing the pattern with a pattern obtained from a normal phenotype; and g) correlating a dissimilar pattern to an aberrant phenotype.

In certain embodiments, analyzing the zones for an indication of a normal or aberrant phenotype comprises the steps of e) identifying a pattern within the markers; f) comparing the pattern with a pattern obtained from an aberrant phenotype; and g) correlating a similar pattern to an aberrant phenotype.

In certain embodiments, analyzing the zones for an indication of a normal or aberrant phenotype comprises the steps of e) identifying a pattern within the markers; f) comparing the pattern with a pattern obtained from an aberrant phenotype; and g) correlating a dissimilar pattern to a normal phenotype.

In certain embodiments, data from analyzing the pattern, e.g., fluorescence changes due to binding of molecules to the tagged glycosphingolipids or tagged glycans, is stored in the memory of a computer. The analysis may be performed, recorded, or displayed on a computer/monitor and one may then report, print, or transfer the results, e.g., in writing or in an electronic document, to a desired recipient or medical professional.

In certain embodiments, the disclosure relates to a glycosphingolipid comprising an aromatic group and a strait chain hydrocarbon with an amine group. The modified glycosphingolipid typically comprises a molecule of formula I:

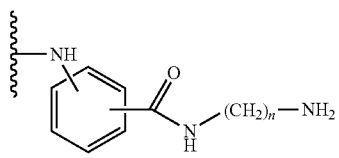

Formula I or salts thereof wherein n is 2, 4, 8 or greater or a glycosphingolipid of formula II,

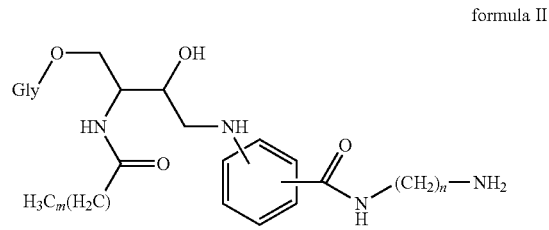

formula II or salts thereof, wherein n is 2, 4, or greater than 4, or 8 or greater, m is greater than 4, 9, 12, or greater than 13, and Gly is a glycan.

In certain embodiments, the disclosure relates to producing a tagged glycosphingolipid and tagged glycan comprising: collecting a sample comprising cells or membrane comprising glycoproteins, glycosphingolipids or other glycolipid: chemically or enzymatically releasing the glycosphingolipids and glycans from the glycoproteins on the exterior of the cells; tagging the glycosphingolipids and glycans; purifying; and conjugating the purified tagged glycosphingolipids and glycans to a solid surface microarray of zones comprising different tagged glycosphingolipids or glycans.

In certain embodiments, the disclosure further comprises exposing the solid surface with zones of immobilized tagged purified glycosphingolipids and glycans to an analyte with glycan adhesion properties, e.g., glycan binding protein, antibody, microbes, toxins, a viral strain, virus particle, virus like particle, bacteria, or other pathogen, and evaluating the zones for binding of the analyte, e.g., by evaluating changes of the fluorescence pattern on the solid surface before and after exposure of the zones to the analyte. The analyte may be evaluated in light of its own binding or how the analyte changes the binding of known binders. It is contemplated that the analyte itself may be conjugated to a fluorescent molecule or fluorescence quenching molecule to the tagged molecule on the immobilized glycosphingolipid or glycan to allow for FRET.

In certain embodiments, the disclosure contemplates any compositions and methods disclosed herein may be utilized to evaluate any glycosphingolipid or glycolipid that contains a double bond.

In certain embodiments, the compositions and methods disclosed herein may be used to identify carbohydrate structures in glycoconjugates associated with human disorders and diseases; identify glycan-binding proteins that recognize carbohydrate structures; identify genes regulating expression of glycoconjugates and glycan-binding proteins; to identify host-pathogen interactions involving glycoconjugates in viral, microbial, and parasitic diseases; and to identify changes in glycosylation associated with heritable and acquired human genetic disorders, e.g., used for diseases and disorders involving altered glycan expression, e.g., CDGs, inheritable diseases, acquired diseases, cancer, IgA nephropathy.

In certain embodiments, the disclosure contemplates methods of diagnosing infections with certain viral strains by creating glycolipid and glycan library with compositions disclosed herein and determining the binding patterns of the virus. Comparing the viral recognition pattern of known strains, e.g., influenza H1N1, H3N2 (Sub7-1 or Sub6-1), to the pattern from a sample from a subject one may identify specific viruses, strains, and subtypes.

In certain embodiments, the disclosure relates to methods of detecting or screening for autoimmune diseases, e.g., Lyme disease, comprising mixing a sample from a subject with glycan epitope of an antibody indicative of the autoimmune disease, e.g., GD1b-Lactone and analyzing whether an antibody to the glycan epitope (anti-glycan antibody), e.g., anti-GD1b-Lactone antibody, in the sample and correlating the absence of binding to glycan epitope to the lack of the autoimmune disease, e.g., Lyme disease, or correlating the binding of an antibody to the glycan epitope to the presence of autoimmune disease, e.g., Lyme disease. Analyzing may be done by detecting or measuring changes of light emission or absorption about the location of the glycan epitope upon binding or other physical phenomena associated with antibody binding. Glycan epitope may be immobilized to a zone, exposed to the sample, e.g., serum, and mixed with a secondary antibody that recognizes the primary antibody. The secondary antibody may contain a marker, e.g., fluorescent molecule. The data from analyzing the binding properties may be recorded in the memory of a computer, displayed on a computer screen, or transmitted by writing or an electronic document to the subject or a medical professional.

In certain embodiments, the disclosure relates to diagnostic kits comprising compositions disclosed herein and optionally a fluid transfer device.

BRIEF DESCRIPTION OF THE FIGURES

FIG. 1 illustrates shotgun glycomics. Glycans are released chemically or enzymatically from glycoproteins. GSLs are modified directly. The fluorescently labeled Glycans and GSLs are separated, quantified, and printed to create microarrays available for interrogation with GBPs.

FIG. 2A illustrates the derivatization of GSLs with a bifunctional linker.

FIG. 2B shows the C18-HPLC profiles of AOAB derivatization of GM1, GD1a, GT1b and BBG mixture detected by fluorescence.

FIG. 2C shows the MALDI-TOF spectra of GM1-AOAB, GD1a-AOAB and GT1b-AOAB purified by HPLC. The spectra were acquired in the reflective negative mode.

FIG. 2D shows the normal phase HPLC profiles of crude ODA treatment of BBG-PNPA conjugates without precipitation, the precipitate, and the filtrate of BBG-PNPA mixture after addition of acetonitrile.

FIG. 3A shows data on the binding assay on the BBG GSL-AOAB microarray prepared from 2D HPLC separation of cholera toxin subunit B (CTSB).

FIG. 3B shows data on the binding assay on the BBG GSL-AOAB microarray prepared from 2D HPLC separation of anti-GD1a antibody.

FIG. 3C shows MS of bound fraction #9.

FIG. 3D shows MS of bound fraction #24.

FIG. 4A shows data with a comparison of IgG binding of sera from Lyme disease patients and control sera (tested at 1:100 dilution). The average RFUs are normalized in each serum sample by setting the binding of fraction 33 in control and patient serum to 100.

FIG. 4B shows data on the distribution of binding by patient and control sera over six selected GSL-AOAB fractions (#12, 17, 26, 33, 39, and 40). Blue squares=individual control sera values, Red circles=individual patient sera values. P values, calculated with Student's t-test, are given for the comparison of control to patient for the selected 6 glycans.

FIG. 4C illustrates the proposed structural characterization of bound fraction #12 by MS and MS/MS. Microarrays from brain gangliosides reveal novel antigen GD1b-Lactone recognized by antibodies in sera from patients with lyme disease.

FIG. 5 illustrates monosialyl ganglioside GM1 (Galβ1-3GalNAcβ1-4(Neu5Acα2-3)Galβ1-4Glcβ1-ceramide) treated with ozone, PNPA, and diamines with different lengths. Treatment of PNPA conjugates with ethylenediamine yielded AEAB conjugates, while treatment with 1,4-diaminobutane and 1,8-diaminooctane (ODA) generated homologs with varied lengths, termed N-(aminobutyl)-2-amino benzamide (ABAB) and N-(aminooctyl)-2-amino benzamide (AOAB) conjugates. The fluorescent GM1 conjugates are named as GM1-AEAB, GM1-ABAB and GM 1-AOAB.

FIG. 6 shows a fluorescent image on a slide spotted with GM1-AEAB, GM1-ABAB and GM1-AOAB.

DETAILED DISCUSSION

Natural glycan array development is a strategy in which glycans derived by enzymatic or chemical cleavage from natural sources are derivatized with a fluorescent linker and separated by multidimensional chromatography to obtain "tagged glycan libraries" or TGLs, and the purified tagged glycans can be printed as glycan microarrays. Reagents for preparing fluorescently labeled glycans from glycoproteins

Shotgun Glycomics

A major hurdle to functional glycomics in general is the challenge of derivatizing glycosphingolipids (GSLs). Glycans of GSLs are linked to a sphingosine moiety, and while enzymatic release of the glycans from GSLs is feasible, the loss of the aglycone may compromise glycan-binding proteins (GBPs) recognition. Therefore, an approach was developed for fluorescently labeling GSLs that permits derivatization, quantification, and separation by HPLC, and immobilization to glass slides to generate GSL shotgun microarrays.

In certain embodiments, the disclosure relates to shotgun glycomics which refers to microarrays obtained from derivatizing glycans from GSLs and glycoproteins to generate fluorescently labeled glycans. These conjugates can be separated, quantified, and covalently printed on glass slides or other surfaces for interrogation by, for example, GBPs and antibodies.

In certain embodiments, the disclosure relates to the use of a fluorescent tag, such as N-(aminoethyl)-2-amino benzamide (AEAB) comprising an available aryl amine for conjugation to free glycans and an alkyl amine for efficient conjugation to reactive surfaces. See Song et al., Chem. Biol. 2009, 4(9), 741-750 and Song et al., Chem Biol, 2009, 16, 36-47, hereby incorporated by reference.

Ozonolysis is specific to unsaturated bonds, as typically occur in sphingosine. Laine et al., J Biol Chem, 1974, 249, 4460-4466. Ozonolysis of sphingosine permits derivatization by PNPA and subsequently diamines to generate glycoconjugates with a functional amino group for subsequent immobilization on reactive surfaces. See, Song et al., 2009, Chem Biol 16, 36-47; Luyai et al., Bioconjug Chem, 2009; Song et al., Glycoconj J, 2008, 25, 15-25; and Xia, et al., Nature methods, 2002, 2, 845-850. By exploiting the alkene present in the sphingosine moiety of most GSLs, the PNPA-diamine labeling procedure was utilized for glycomic analysis of GSLs. In shotgun glycomics, the fractions, which are printed at equimolar concentrations on a microarray, are interrogated with biologically-relevant GBPs, so that structural analyses will be focused on only those glycans recognized by the GBP. Thus, with nanomolar levels of GSL-AOAB purified from natural sources, it is possible to study the binding properties of proteins or microorganisms to different GSL-AOABs by microarray technology.

Studies herein indicate that sera from patients with Lyme disease (borreliosis) express anti-glycolipid antibodies. Lyme disease is initiated from a bacterial infection with *Borrelia burgdorferi*, but the pathogenesis is believed to be related to autoantibodies towards glycolipids. The observed IgG response to a disialylated ganglioside GD1b-lactone in BBG presumably arises from cross reactivity of the IgG generated against the bacterial infection, since glycolipid antigens are known to be present in *B. burgdorferi*. The characterization of GD1b-lactone provides a structural hint for future studies on the pathogenesis of Lyme disease. Similarly, GSL microarrays and TGLs prepared from human erythrocytes and PC3 cells indicate that our approach are useful in identifying anti-carbohydrate antibodies to human tumors and are important in biomarker discoveries for diagnostics and treatments.

TERMS

A "subject" refers to any animal such as a human patient, livestock or a domestic pet.

As used herein a "sample" refers to a composition taken from or originating from a subject. Examples of samples include cell samples, blood samples, tissue samples, hair samples, and urine or excrement samples.

As used herein, the term "marker" is used broadly to encompass a variety of types of molecules which are detectable through spectral properties (e.g., fluorescent markers or "fluorophores") or through functional properties (e.g., affinity markers). A representative affinity marker includes biotin, which is a ligand for avidin and streptavidin. An epitope marker is a marker functioning as a binding site for antibody. Since chimeric receptor proteins and antibodies can be produced recombinantly, receptor ligands are effective affinity markers.

An "aromatic" group refers to a molecular ring structure with atoms in a sp2 hybridized state that provide a delocalized conjugated electron system with an even number of delocalized electrons, but not a multiple of 4. As used herein, it is intended to include heterocyclic or non-heterocyclic aromatic groups. The group may have multiple rings and some of the rings may not be aromatic provided at least one ring is aromatic.

"Chromatography" refers to processes used to purify individual components from mixtures by passing a mixture contained in a "mobile phase" through a "stationary phase," which separates the analyte to be measured from other components in the mixture. A "separation medium" refers to the stationary phase or adsorbent. In certain embodiments, the disclosure relates to analysis of samples using chromatographic processes.

Ion exchange chromatography, liquid chromatography, normal-phase (NP) and reversed-phase chromatography (RP), affinity chromatography, and expanded bed adsorption (EBA) chromatograph all use separation mediums. In ion exchange chromatography, the separation medium is typically an ion exchange resin that carries charged functional groups which interact with oppositely charged groups of the compound to be retained. In affinity chromatography, the separation medium is typically a gel matrix, often of agarose, typically coupled with metals or molecules that bind with markers or tags such antigens, antibodies, enzymes, substrates, receptors, and ligands. Methods utilizing antibodies or antigens (epitopes) coupled to the separation medium is typically referred to as immunoaffinity chromatography and the separation medium is referred to as an immunoabsorbant.

Liquid chromatography (LC) is a separation technique in which the mobile phase is a liquid. Typical separation mediums for liquid column chromatography include silica gel, alumina, and cellulose powder. Liquid chromatography carried out under a relatively high pressure is referred to as high performance liquid chromatography (HPLC). HPLC is historically divided into two different sub-classes based on the polarity of the mobile and stationary phases. The technique in which the stationary phase is more polar than the mobile phase (e.g. toluene as the mobile phase, silica as the stationary phase) is called normal phase liquid chromatography (NPLC) and the opposite (e.g. water-methanol mixture as the mobile phase and $C_{18}$=octadecylsilyl as the stationary phase) is called reversed phase liquid chromatography (RPLC).

GSL refers to a glycosphingolipid. AEAB refers to N-(2-aminoethyl)-2-amino-benzamide. GSL-AEAB refers to a Glycosphingolipid-AEAB conjugate. ABAB refers to N-(aminobutyl)-2-amino benzamide. AOAB refers to N-(aminooctyl)-2-amino benzamide. TGL refers to tagged GSL/glycolipid library or tagged glycan library. ConA refers to Concanavalin A. CTSB refers to Cholera toxin subunit B. MAA refers to *Maackia amurensis* agglutinin. NHS refers to N-hydroxysuccinimide. RFU refers to relative fluorescence unit. TLC refers to thin layer chromatography. AAL refers to *Aleuria aurantia* agglutinin. UEA-I refers to *Ulex europaeus* agglutinin I. HPA refers to *Helix pomatia* agglutinin. BBG refers to Bovine brain gangliosides. LNnT refers to Galβ1-4GlcNAcβ1-3Galβ1-4Glc. LNFIII refers to Galβ1-4(Fucα1-3)GlcNAcβ1-3Galβ1-4Glc. Le$^y$Le$^x$ refers to Fucα1-2Galβ1-4(Fucα1-3)GlcNAcβ1-3Galβ1-4(Fucα1-3)GlcNAc. Man5 refers to Manα1-6(Manα1-3)Manα1-6(Manα1-3)Manβ1-4GlcNAcβ1-4GlcNAc. NA2 refers to Galβ1-4GlcNAcβ1-2Manα1-6(Galβ1-4GlcNAcβ1-2Manα1-3)Manβ1-4GlcNAcβ1-4GlcNAc.

As used herein the term "tag" or "tagged" molecule refers to a molecule that will photoluminescence, i.e., emit light as a result of the absorption of photons, e.g., fluorescence or phosphorescence.

EXPERIMENTAL

Example 1

Ozonolysis and Fluorescent Conjugation

GSLs (0.1-10 mg) were dissolved in 1-2 ml chloroform/methanol=2/1 (v/v) and chilled in a dry ice/acetone bath. Ozone freshly generated by the ozone generator was passed through the solution for 1 min, while the blue color persisted. Nitrogen was bubbled through the solution for 1 min to remove the excess ozone. Methyl sulfide (Me$_2$S), 100 μl, was added to destroy residual ozone; and after standing for 1 h at room temperature, the solution was dried under a stream of nitrogen.

The ozonolysis products were labeled with p-nitrophenyl anthranilate (PNPA) as described for free glycans in Luyai et al, Bioconjug Chem, 2009, 20 (8), 1618-1624. Briefly, 0.35 M PNPA and 1 M NaCNBH$_3$ in DMSO/AcOH (7:3 v/v) were freshly prepared, and an equal amount (20 to 200 μl) of each solution was added to the dried residue and heated at 65° C. for 2 h. Acetonitrile (10 volumes) was added and the mixture was cooled at −20° C. for 2 h. The mixture was centrifuged and the supernatant was removed. To the precipitated GSL-PNPA derivatives, ODA (10% in DMSO, 20 to 200 μl) was added and the suspension was mixed on a vortex mixer for 30 minutes followed by the addition of 20 to 200 μl of 10% acetic acid. The mixture was centrifuged and the product was obtained from the supernatant.

Figure 2A:
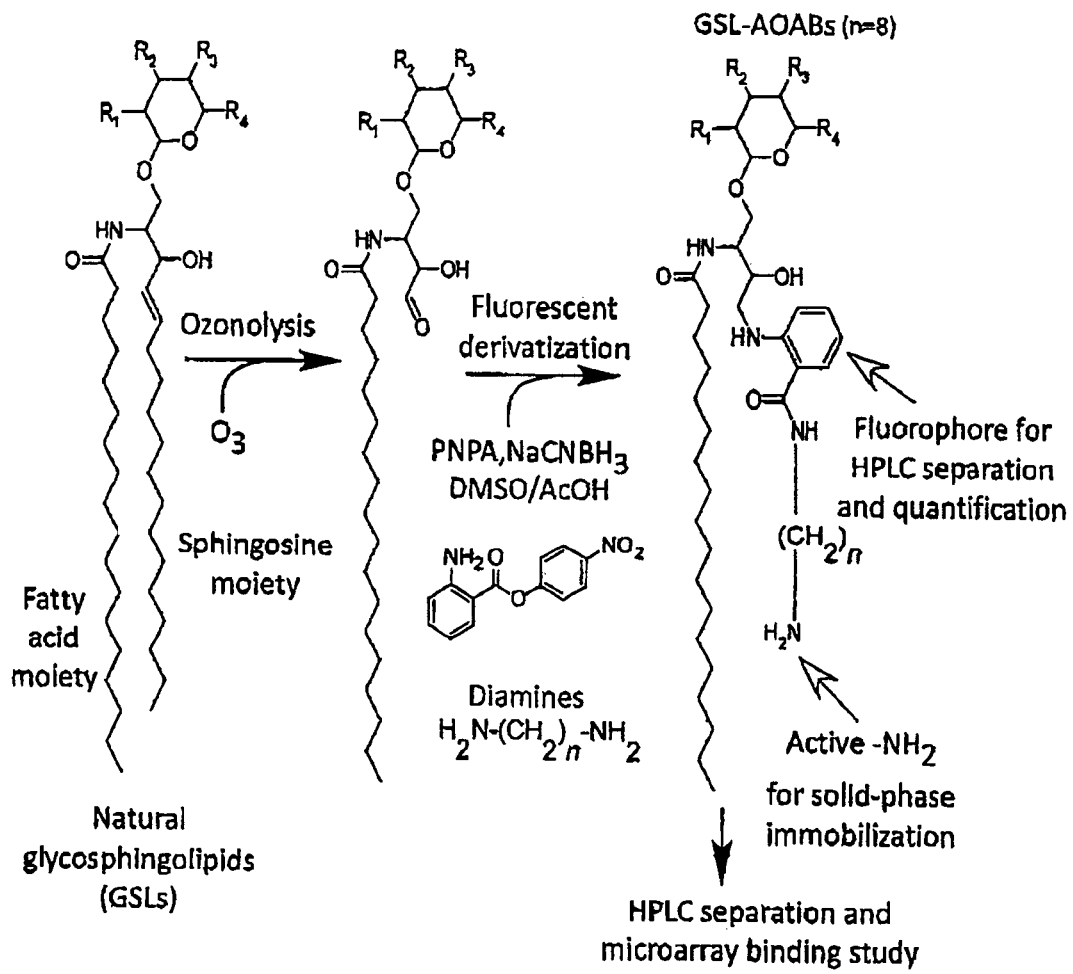

Ozonolysis of the common sphingosine moiety in GSLs generates a free aldehyde, readily reactive with the heterobifunctional p-nitrophenyl anthranilate (PNPA) through reductive amination to form a GSL-PNPA derivative, bearing a p-nitrophenyl ester as an excellent leaving group (FIG. 2A). The derivative precipitates from the product mixture with acetonitrile, and upon reaction with diamines, transforms to a fluorescent labeled GSL derivative, which retains an alkyl amine that can be covalently coupled to appropriate reactive surfaces.

Example 2

Printing, Binding Assay, and Scanning

Figure 5:
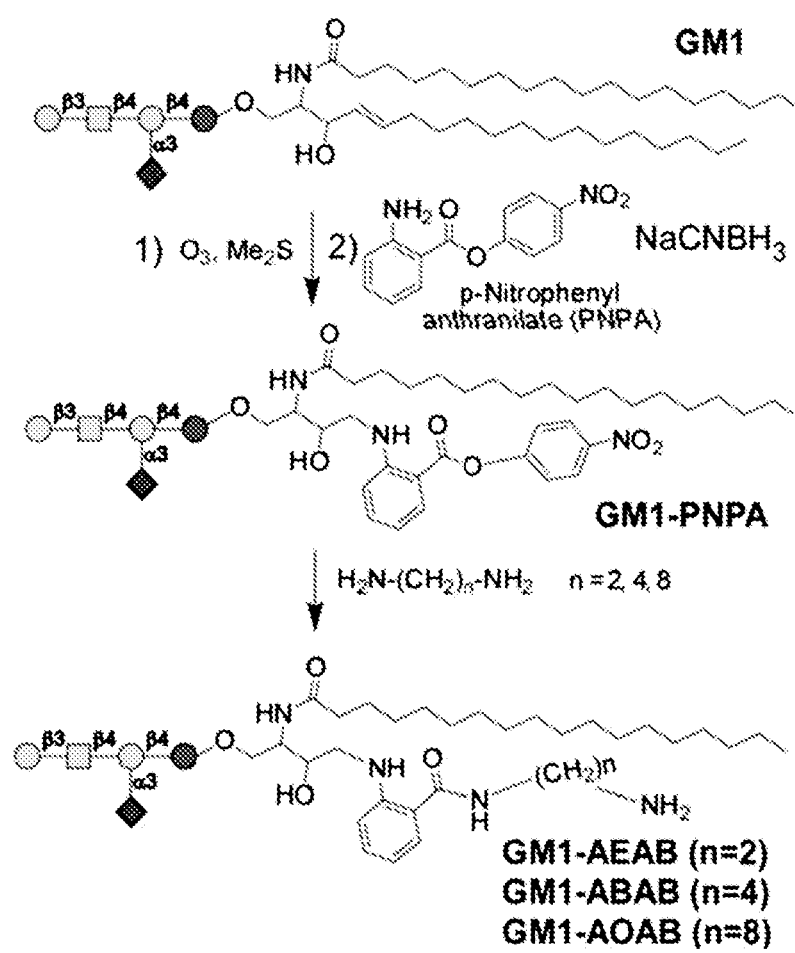

The approach was evaluated and optimized using the monosialyl ganglioside GM1 (Galβ1-3GalNAcβ1-4(Neu5Acα2-3)Galβ1-4Glcβ1-ceramide) (FIG. 5). The monosialyl ganglioside GM1 (Galβ1-3GalNAcβ1-4(Neu5Acα2-3)Galβ1-4Glcβ1-ceramide) is treated with ozone, PNPA, and diamines with different lengths. Treatment of PNPA conjugates with ethylenediamine yielded AEAB conjugates, while treatment with 1,4-diaminobutane and 1,8-diaminooctane (ODA) generated homologs with varied lengths, termed N-(aminobutyl)-2-amino benzamide (ABAB) and N-(aminooctyl)-2-amino benzamide (AOAB) conjugates. The fluorescent GM1 conjugates are named as GM1-AEAB, GM1-ABAB and GM1-AOAB. C18-HPLC profiles of GM1-AEAB, GM1-ABAB and GM1-AOAB products gave a single fluorescent product peak by C$_{18}$-HPLC. MALDI-TOF profiles of GM1-AEAB, GM1-ABAB and GM1-AOAB, showed masses matching calculated values.

Figure 6:
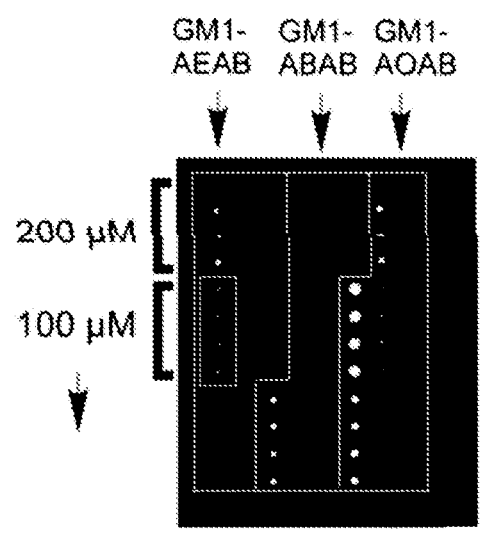

The test printing of GM1-AEAB, GM1-ABAB and GM1-AOAB at different concentrations is shown in FIG. 6. The three GM1 derivatives were quantified based on fluorescence, printed on three different glass slides, and interrogated with biotinylated cholera toxin subunit B (CTSB), which specifically binds the GM1 glycan. They were printed on 4 slides: nitrocellulose-vendor 1, nitrocellulose-vendor 2, NHS and epoxy slides. For each sample, 8 concentrations (200, 100, 50, 25, 12.5, 6.25, 3.13, 1.6 μM) were printed in replicates of n=4 for each concentration. The slides were interrogated with biotinylated CTSB and detected by cyanine 5-streptavidin. The slides were scanned at different photomultiplier tube (PMT) settings. PMT 70 has higher detecting sensitivity than PMT 50. For nitrocellulose slides, lower PMT (50) had to be used due to the autofluorescence of nitrocellulose membrane. For glass slides, either NHS or epoxy, higher PMT (70) was used to reach a higher sensitivity. When background is high, lower PMT (50) can be used to reduce the background.

The comparative studies by printing of the three GM1 derivatives on nitrocellulose slides and NHS- or epoxy-slides demonstrate that the N-(aminooctyl)-2-amino benzamide (AOAB) conjugates, GM1-AOAB with the C$_8$ extension was detected by CTSB with greater sensitivity than the other derivatives. The longer alkyl chain of GM1-AOAB, which increases its hydrophobicity, may increase the printing efficiency or, more possibly, may help to organize the parallel fatty acid chain, reducing its interference between binding of CTSB and glycan.

Figure 2B:
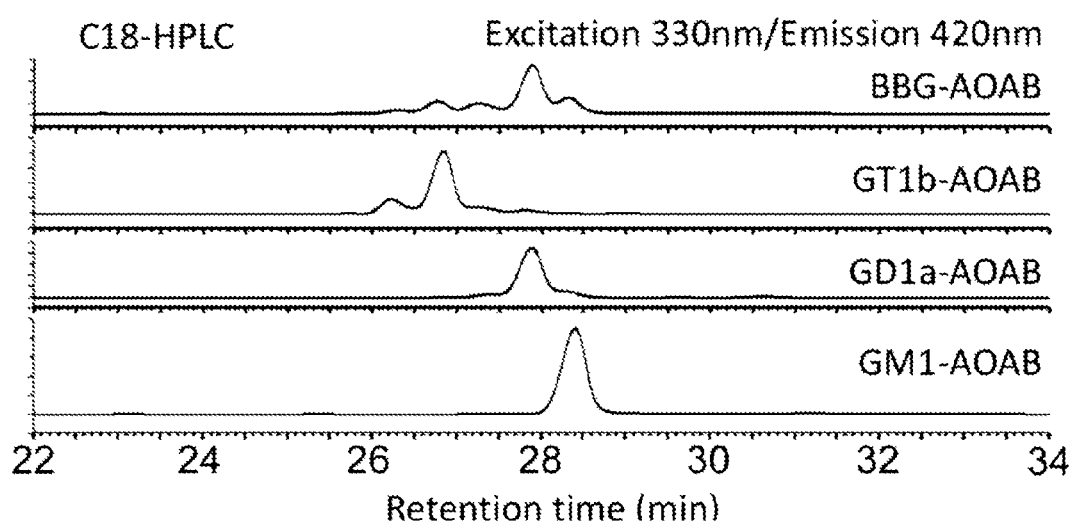
Figure 2C:
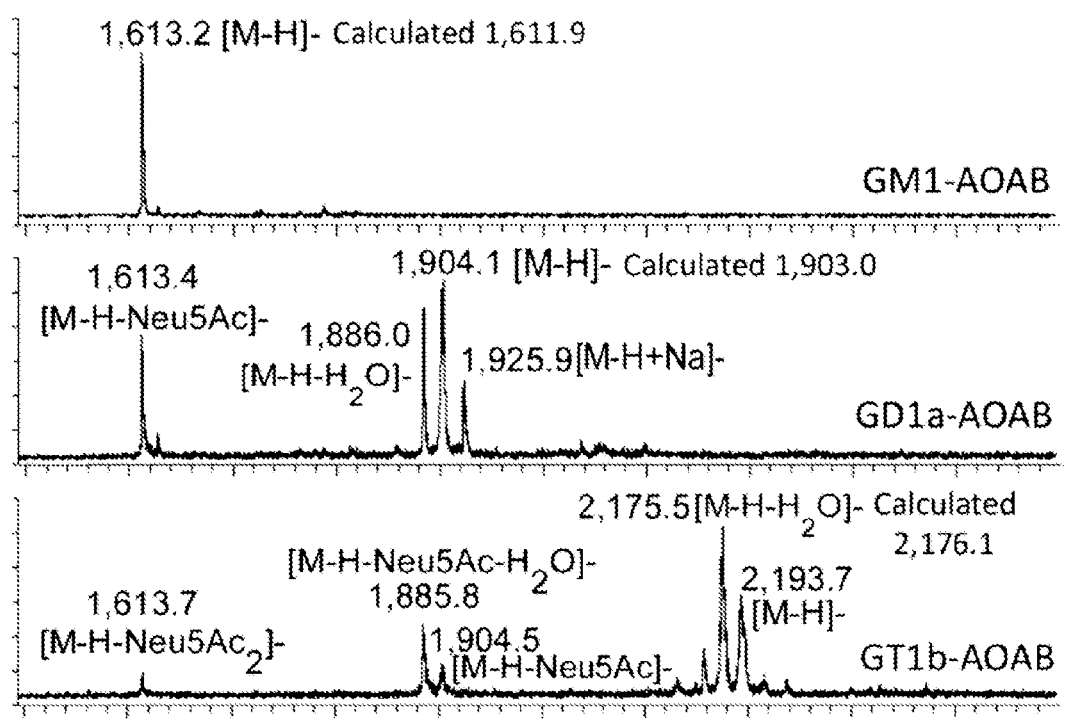
Figure 2D:
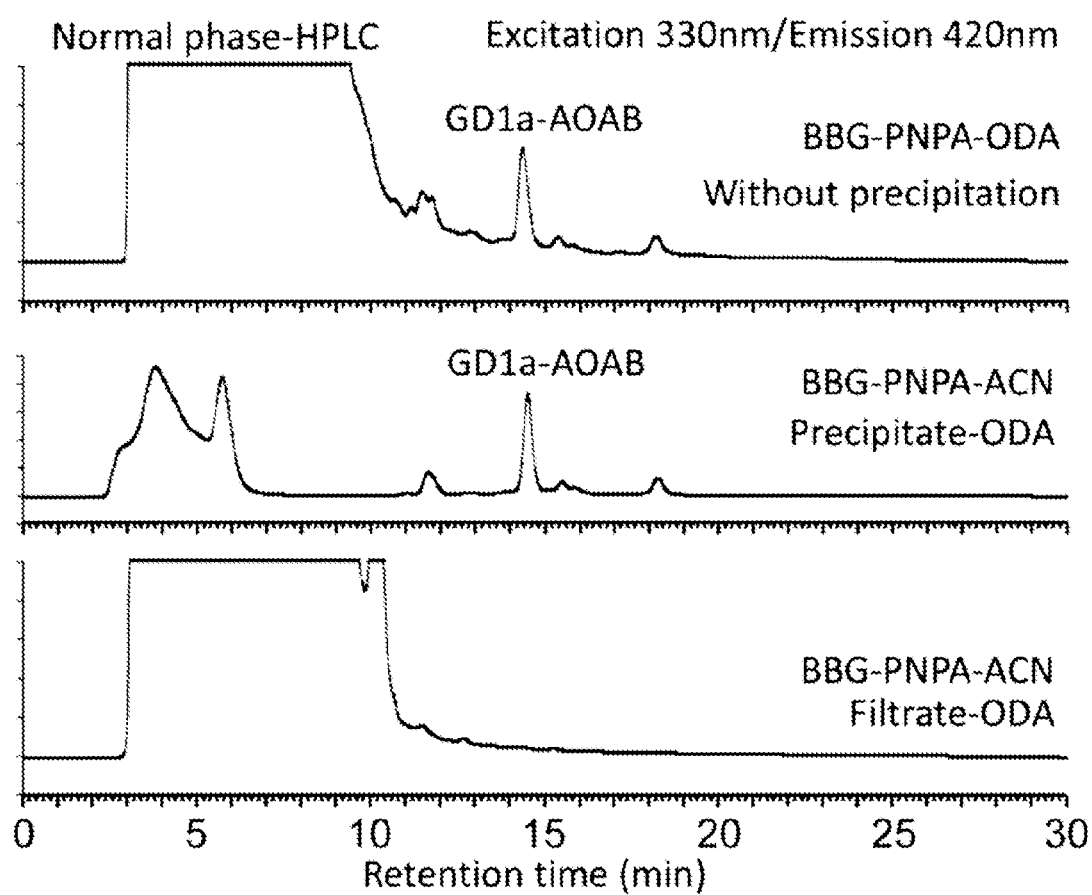

NHS-activated slides were used for further studies, due to their generally lower background, and the ozone, PNPA, and octane-1,8-diamine (ODA) derivatization with its C$_8$ extension, due to its relatively higher sensitivity of detection on microarray. This procedure was evaluated with other GSLs, including GD1a, GT1b, and a mixture of bovine brain gangliosides (BBG) (FIG. 2B-D). C$_{18}$-HPLC profiles (FIG. 2B) of the products from GM1, GD1a, and GT1b each show a dominant fluorescent peak, suggesting that the reactions are highly specific. No substantial desilylation occurred for individual gangliosides or the BBG mixture based on HPLC. Products were purified by HPLC and characterized by MALDI-TOF (FIG. 2C) and confirmed expected masses. Partial loss of sialic acids was observed in the MALDI process, especially for multi-sialylated gangliosides.

To evaluate whether precipitation of GSL-PNPA in acetonitrile after reductive amination was quantitative, the filtrate (FIG. 2D, bottom profile), precipitate (FIG. 2D, middle profile), and crude reductive amination product without precipitation (FIG. 2D, top profile) were treated with a large excess of ODA. Comparison of HPLC profiles of the products suggests that the precipitation is complete. The underivatized GSLs and GSL-AOAB products were then compared using TLC. Both underivatized GSLs and the GSL-AOAB products were detected with orcinol staining, while only the AOAB derivatives showed fluorescence under UV light. The orcinol staining suggested the nearly quantitative AOAB-derivatization, since the TLC profiles after derivatization did not show more complexity. The fluorescent nature of the derivatives greatly facilitates preparative TLC and TLC protein overlay without destructive chemical staining.

An HPLC CBM-20A system (Shimadzu), coupled with a UV detector (SPD-20A) and a fluorescence detector (RF-10Ax1), was used for HPLC analysis and separation of GSL-AOABs. UV absorption at 330 nm or fluorescence at 330 nm excitation and 420 nm emission was used to detect GSL-AOABs in HPLC analyses and separations. Both UV absorption and fluorescence intensity were used for the quantification of GSLs with LNnT-AEAB as a standard.

For normal phase HPLC separation, a Zorbax $NH_2$ column (250 mm×4.6 mm) was used for analysis and a semi-preparative Zorbax $NH_2$ column (250 mm×9.2 mm) was used for preparative separations. The mobile phase used was acetonitrile, water, and 250 mM ammonium acetate (pH 4.5). In the analytical run, the concentration of water increased from 20% to 50% and the concentration of ammonium acetate buffer increased from 0 mM to 50 mM linearly over 25 min. In the preparative run, the concentration of water increased from 10% to 90% and the concentration of ammonium acetate buffer increased from 0 mM to 100 mM linearly over 120 min. For reverse phase HPLC with $C_{18}$ column, a Vydac $C_{18}$ column (250 mm×4.6 mm) was used. The mobile phase was acetonitrile and water with 0.1% trifluoroacetic acid (TFA). The concentration of acetonitrile increased from 15% to 90% linearly over either 37.5 or 75 min.

NHS-activated slides were purchased (Schott). Epoxy slides were purchased (Corning). Non-contact printing was performed using a Piezoarray printer (Perkin Elmer). The average spot volume was within 10% variation of ⅓ mL. All samples were printed in phosphate buffer (300 mM sodium phosphates, pH 8.5). The processing for NHS and epoxy slides is described below. After printing, the slides were boxed loosely and put in a high moisture chamber at 50° C. and incubated for 1 h. The slides were washed and blocked with 50 mM ethanolamine in 0.1 M Tris buffer (pH 9.0) for 1 h. The slides were dried by centrifugation and stored desiccated at −20° C. for future use. Before assay, the slides were rehydrated for 5 min in TSM buffer [20 mM Tris-HCl, 150 mM sodium chloride (NaCl), 0.2 mM calcium chloride ($CaCl2$), and 0.2 mM magnesium chloride ($MgCl2$)]. Biotin-hydrazine was printed as a positive control and also used for grid localization.

The slides were scanned with a ProScanarray microarray scanner (Perkin Elmer) equipped with 4 lasers covering an excitation range from 488 nm to 637 nm. The scanned images were analyzed with ScanArray Express software. For cyanine 5 fluorescence, 649 nm (Ex) and 670 nm (Em) were used. For Alexa488 fluorescence, 495 nm (Ex) and 519 nm (Em) were used. All images obtained from the scanner were in grayscale and colored for easy discrimination.

Example 3

Shotgun GSL Microarray Generated from Bovine Brain Gangliosides (BBG)

BBG were treated with ozone, PNPA, and ODA. The AOAB-labeled mixture of fluorescent GSLs from excess reagents were separated by semi-preparative $C_{18}$ HPLC and further fractionated by 2D-HPLC. The normal phase columns retain GSL-AEABs via their glycan moieties and provide good separations. The normal phase fractions are further resolved in a 2nd dimension by reverse phase HPLC, which simultaneously desalts each of the normal phase fractions. The resolved GSL-AOAB derivatives comprise the Tagged Glycolipid Library (TGL) and possess a free alkyl-amine function for printing as a GSL microarray and subsequent MS characterization.

Figure 3A:
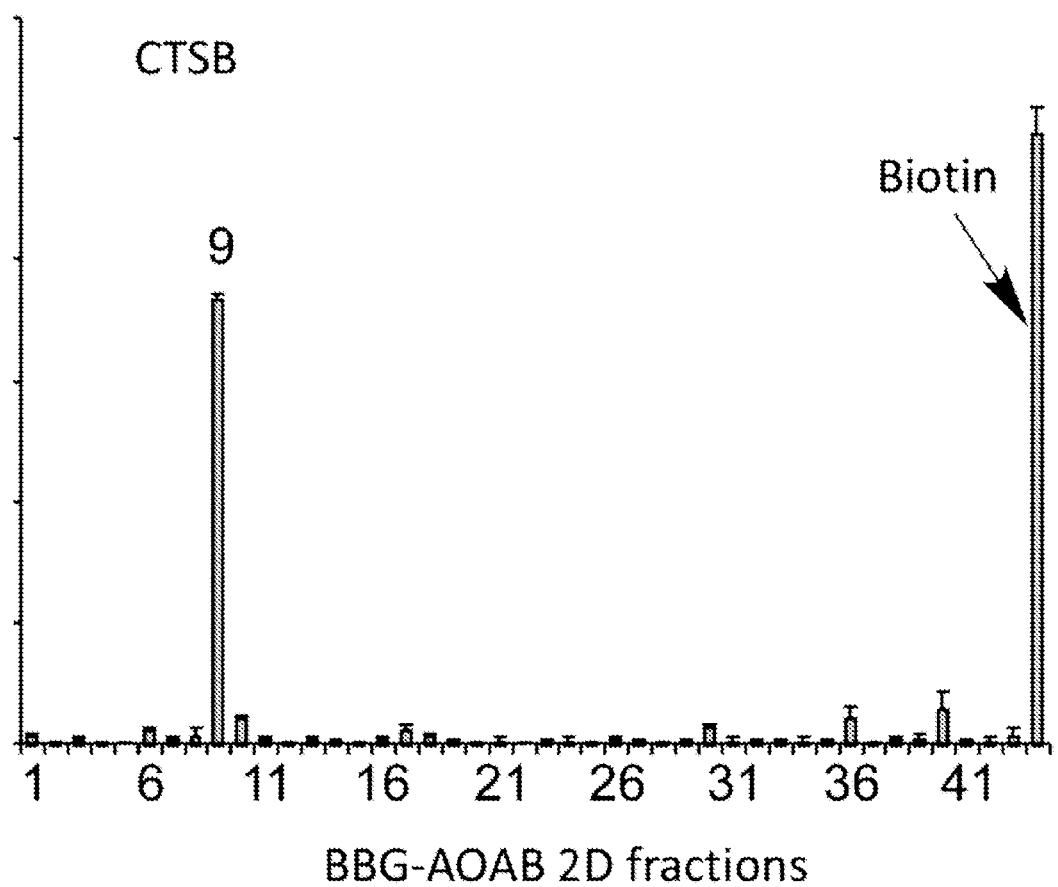
Figure 3B:
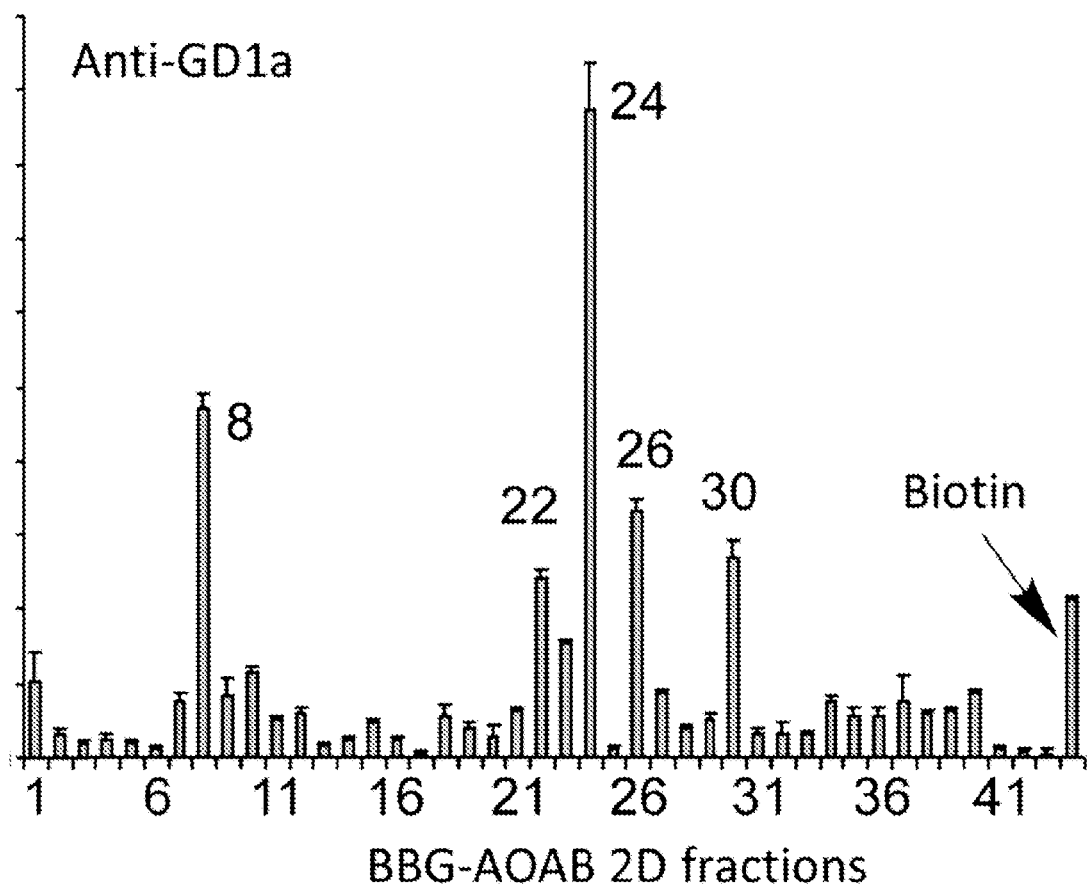
Figure 3C:
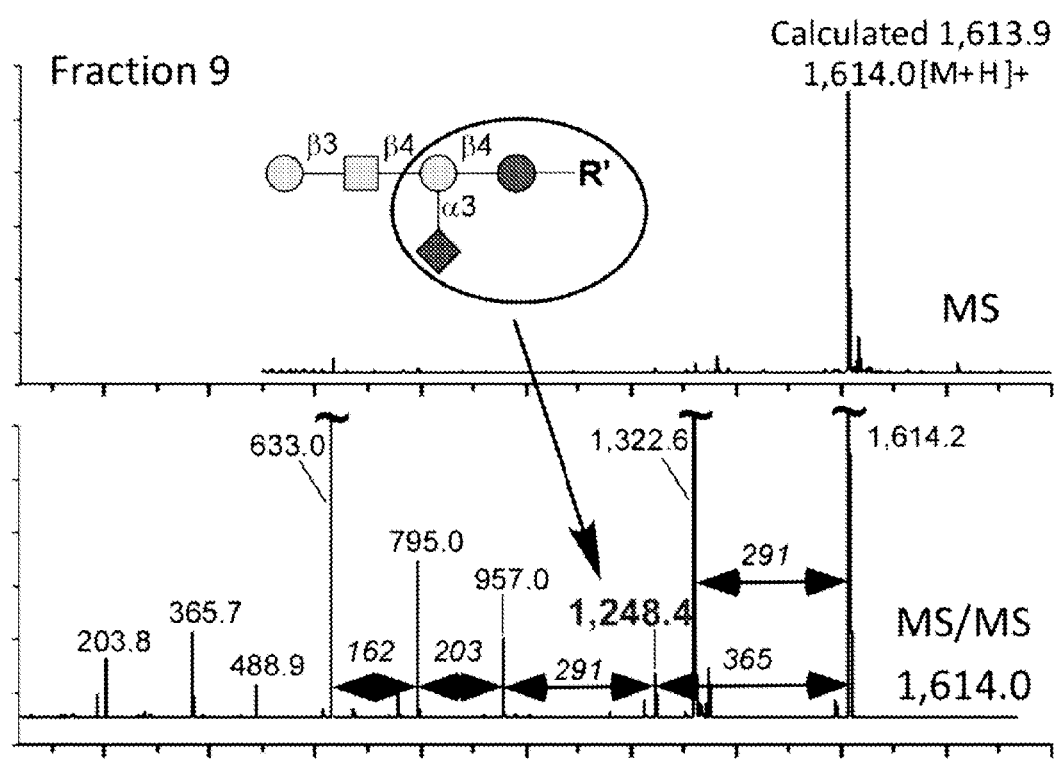

Equimolar concentrations (10 µM) of the recovered peaks were quantified, characterized and printed on NHS-slides. This BBG microarray contains 40 GSL-AOAB fractions plus controls. The compositional information of these fractions from MALDI-TOF/TOF was generated in an automatic fashion. This GSL shotgun microarray was interrogated with biologically-relevant GBPs: cholera toxin subunit B (CTSB) (FIG. 3a), and anti-GD1a antibody (FIG. 3b). These GBPs primarily bound GSLs in fractions #9 and #24, respectively. The glycan structures were characterized in these fractions by MS and MS/MS (FIG. 3c,d). The parent ions matched the expected compositions, which were subjected to collision-induced dissociation MS/MS analysis for more detailed structural analysis. The loss of labile Neu5Ac (−291) gave abundant fragment ions. Furthermore, the sequential loss of Hex (−162), HexNAc (−203), Hex (−162), Hex (−162) in the MS/MS spectra of fractions #9 and #24 is consistent with the structure asialoGM1, Galβ1-3GalNAcβ1-4Galβ1-4Glcβ1-R, confirming the general ganglioside core structure. Further, the fragment ion at 1248 (1247 for fraction #24) identifies Neu5Ac-Gal-Glc-ceramide-AOAB, and excludes the possibility of other isomers, such as GM1b and GD1b. The results allow the predictions that fraction #9 is GM1-AOAB, whereas fraction #24 is GD1a-AOAB (Neu5Acα2-3Galβ1-3GalNAcβ1-4 (Neu5Acα2-3)Galβ1-4Glcβ1-R). The anti-GD1a antibody also exhibited cross-reactivity to other fractions (#8, #22, #26, #30). This result highlights the value of the GSL shotgun microarray to explore the specificities of monoclonal antibodies.

Example 4

Serum Antibody Binding to Shotgun GSL Microarray

Figure 3D:
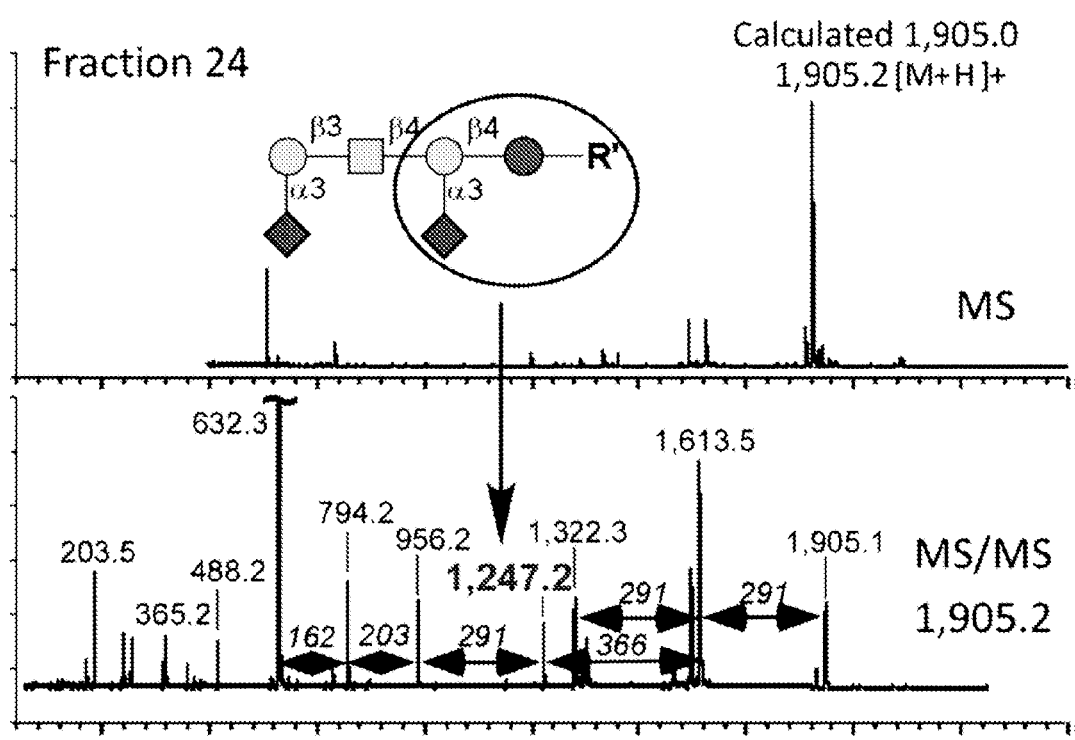
Figure 4A:
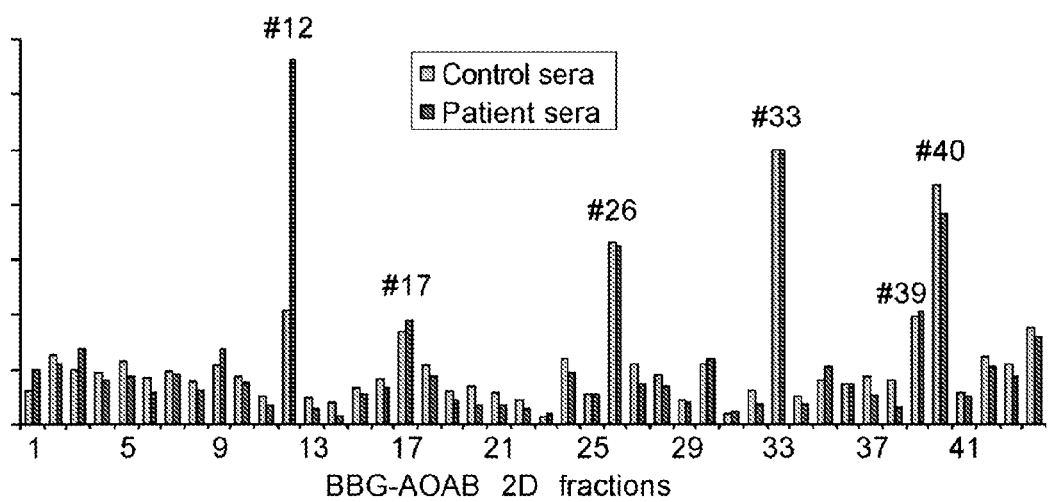
Figure 4B:
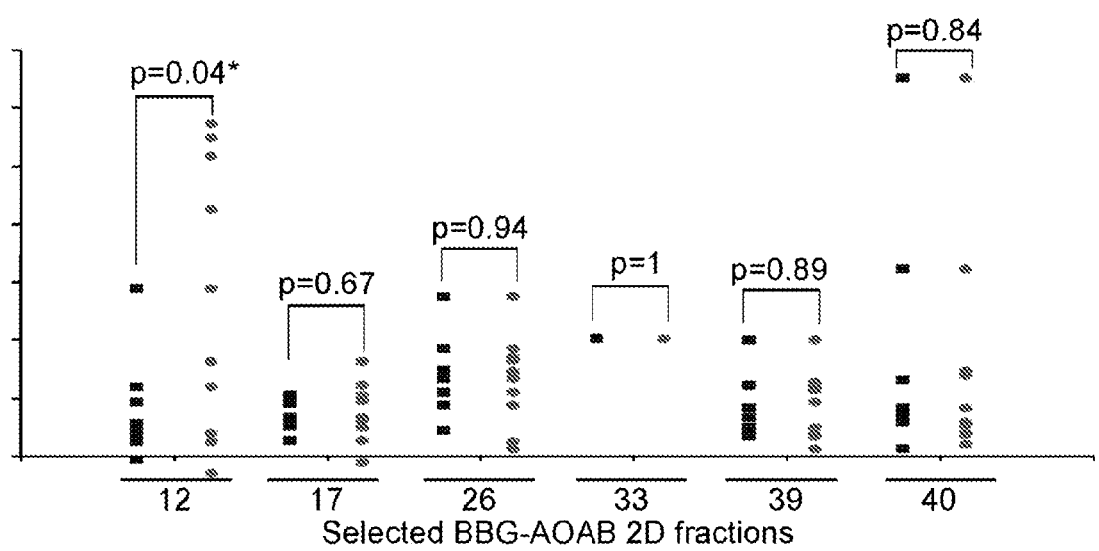
Figure 4C:
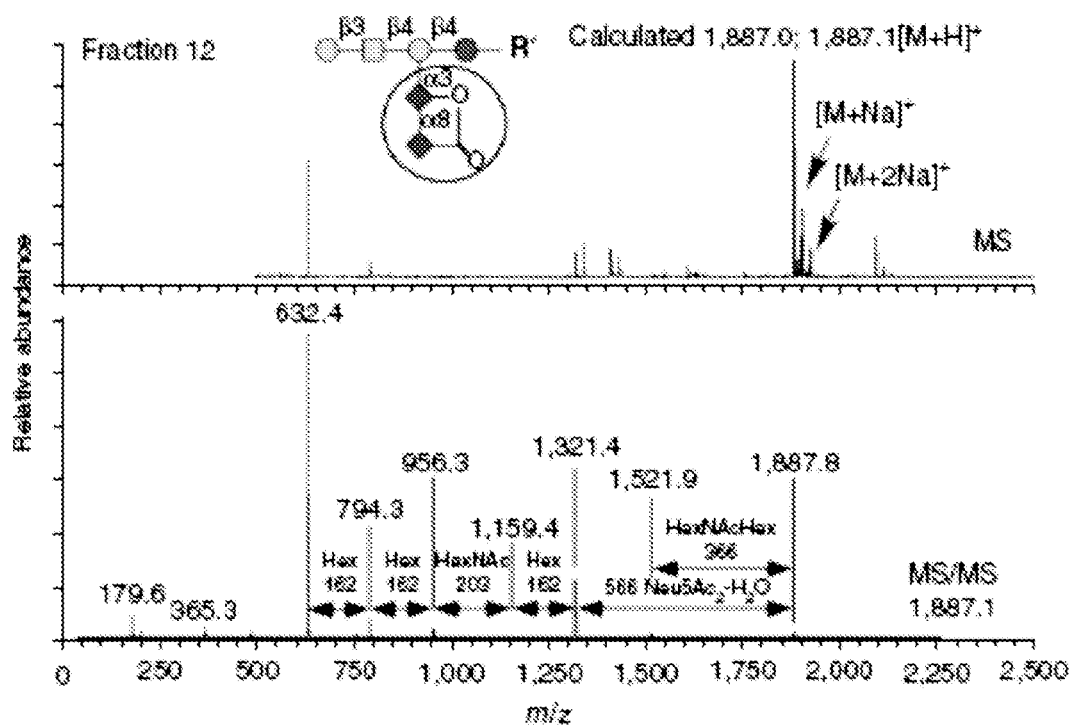

To further evaluate the general utility of this approach using the BBG microarray, serum was screened with anti-GSL antibodies from patients diagnosed with Lyme disease (FIG. 4a,b). Studies show a variety of peripheral neuropathies, including those linked with Lyme disease, are associated with antiganglioside antibodies. While both control and Lyme sera showed comparable weak binding to several gangliosides, only one BBG fraction (#12) showed statistically significant recognition by patient sera ($P<0.05$) compared to control sera (FIG. 4b). Out of 10 patients, 5 showed a relatively high IgG response (>100 normalized relative fluorescence units, RFU) and 2 showed medium IgG response (50-100 normalized RFU) against fraction #12. Only 1 of 8 control sera showed a high IgG response and 1 showed a medium level IgG response against fraction #12. The MS and MS/MS data of fraction #12 was analyzed (FIG. 4c) suggesting a composition of (Hex)3(HexNAc)1(Neu5Ac)2-H2O. MS/MS confirmed the composition with a clear Hex-Hex-HexNAc-Hex pattern, consistent with a ganglioside tetrasaccharide. The neutral loss of H2O may have occurred during ionization; however considerably shorter retention time (34.76 min) of this derivative compared to standard GD1a-AOAB's (40.46 min) on normal phase HPLC suggests lower hydrophilicity, which might result from dehydration within the molecule. Although fraction #12 is a disialyl ganglioside, its MS/MS pattern is dramatically different from that of GD1a-AOAB, for example (FIG. 3d). There is an abundant fragment ion at 1321.4 from loss of two Neu5Acs (Neu5Ac2-H2O), but absolutely no fragment ion was observed due to loss of one Neu5Ac, suggesting another linkage between the two Neu5Ac moieties besides the common α2,8 glycosidic bond, possibly through formation of an internal ester or anhydro ether bond. Furthermore, the fragment ion at 1521.9, due to loss of HexNAc-Hex without loss of Neu5Ac, indicates no terminal Neu5Ac attached to the far most Gal at the non-reducing end and suggests a structure closely related to GD1b. Further studies including comparison with GD1b-AOAB prepared from standard, neuraminidase resistance, and formation of an amide with ethylenediamine strongly support the prediction that fraction #12 is GD1b-lactone. GD1b-lactone has been identified in brain tissues and melanoma cells. See Terabayashi & Kawanishi, Carbohydr Res, 1998, 307, 281-290 and Riboni et al., J Biol Chem, 1986, 261, 8514-8519. It can also be generated under acidic conditions in vitro. Bassi et al., Carbohydr Res, 1989, 193, 141-146.

Antibodies (anti-GD1a: Millipore, and anti-Blood group A: Santa Cruz Biotechnology) were detected by Alexa488-labeled corresponding secondary antibodies (5 µg ml-1, Invitrogen). For multi-panel experiments on a single slide, the array layout was designed using Piezoarray software according to the dimension of a standard 16-chamber adaptor.

Example 5

Shotgun Glycomics of GSLs from Erythrocytes and PC3 Cells

The extraction and desalting of GSLs from cells essentially followed protocols described in Schnaar, Methods Enzymol, 1994, 230, 348-370. Erythrocyte ghosts were prepared from ~300 ml each of A-type blood and O-type blood. Human erythrocytes contain minute amounts of GSLs expressing blood group antigens, as most blood group antigens are found in glycoproteins. GSLs were extracted from erythrocyte ghosts and subjected to AOAB derivatization. The $C_{18}$-HPLC profiles of O- and A-erythrocyte GSL-AOAB are similar. The TGL of O-erythrocyte GSL-AOAB and A-erythrocyte GSL-AOAB were comprised of 23 and 25 fractions, respectively. After separation and quantification, the TGL shotgun arrays were printed and interrogated with several GBPs. Binding by AAL, specific for α-linked fucose, suggested the general occurrence of fucose, while binding of several fractions by UEA-1, specific for α1-2 fucose, in both O-erythrocytes and A-erythrocytes, indicated the occurrence of H-antigen in both blood types. Interestingly, HPA, specific for terminal α-GalNAc, and anti-blood group A antibody showed binding only to several GSL-AOAB fractions prepared from A-erythrocytes with no cross reactivity to O erythrocytes GSL-AOAB fractions.

Many antibodies and other GBPs recognize tumor cells and may be useful in diagnostics and therapeutics. The shotgun glycomics approach was tested with the cultured prostate cancer cell line PC3, which has been used for immunizations to develop antibodies that may have therapeutic potential and recognize undefined glycolipid antigens. Whole PC3 cell pellet (~0.5 ml, cell count ~5×10$^7$) was directly processed as described below. The wet human erythrocyte ghost pellet (or PC3 whole cell pellet) was homogenized with 3 volumes of water using a tip sonicator. The homogenate was added to 10.7 volumes of methanol slowly with stirring followed by 5.3 volumes of chloroform so that the final solvent ratio is 4:8:3 (C:M:W). The mixture was stirred for 30 min and centrifuged at 8,000×g for 30 min. The supernatant was poured into a separation funnel and 0.173 volume (relative to the supernatant) of water was slowly added. After gentle mixing, the upper phase was isolated. The upper phase was desalted with $C_{18}$ Sep-pak, evaporated and redissolved in chloroform/methanol=2/1 (v/v) for AOAB labeling.

Using 1×10$^7$ PC3 cells, a mixture of GSL-AOAB derivatives were prepared as described above from GSLs extracted from the whole cell pellet. The $C_{18}$-HPLC profile is quite different from that of erythrocytes. Thirty-three fractions were collected, printed on a microarray, and assayed with several plant lectins, showing differential binding to different fractions and controls. Biotinylated lectins (Vector Labs) and CTSB (Sigma) were used in the binding assay and the bound lectins were detected by a secondary incubation with cyanine 5-streptavidin (5 µg ml-1, Invitrogen).

Ten major fractions were characterized by MALDITOF/TOF. Overall, the results predict that sulfated globosides (HexNAc-Hex-Hex-Hex-ceramide) are the major structures in PC3 GSL-AOABs, along with sialylated globosides. Analysis of fraction (#16) illustrates the sulfated globoside structure of the PC3 GSLs. The MS and MS/MS analyses using both positive and negative modes suggest a globo-series GSL structure with a sulfated pentasaccharide glycan. The GSL-AOAB fractions can be processed in a second dimension to generate individual glycans, whose composition can be determined by MS and MS/MS and printed as a microarray to further explore the specificities of antibodies against PC3 cells, such as the F77 antibody that is presumably directed against glycolipid epitopes.

Example 6

Probing Virus-Glycan Interactions Using Glycan Microarrays

Heimburg-Molinaro et al., Methods Mol Biol. 2012; 808:251-67, hereby incorporated by reference provide probing virus-glycan interactions using microarrays. The following may be applied to glycan and GSL micro arrays disclosed herein.

I) Fluorescent Labeling of Virus—
1. Prepared Influenza virus (for example, virus isolated from MDCK cells, purified by sucrose gradient centrifugation, checked for purity by SDS-PAGE, quantified by hemagglutination (HA) assay and/or total viral protein) (BioRad Protein Assay or quantitative SDS-PAGE).
  (a) Virus is grown in LLC-MK2 cells (hPIVs) or MDCK (influenza) in infection medium [DMEM/Ham's F12 (Gibco) supplemented with 1% ITS+(BD) and 0.1% gentamicin (Sigma)]. For influenza, 0.5 µg/mL trypsin (TPCK treated, Worthington) is added to infection medium. For hPIV1 and -2, add 1 µg/mL trypsin to the infection medium.
  (b) Virus is purified by a low speed spin first to remove cell debris, then by pelleting virus from the clarified medium at 52,112×g for 2 h (Beckman L-80 ultracentrifuge, SW-28 rotor), resuspending overnight in calcium-magnesium saline (50 µL per pellet), then centrifugation through a 10-60% sucrose gradient (hPIV) or 10-40% (influenza) (Beckman TL-100 ultracentrifuge, TLS-55 rotor, gradient at 105,000×g for 15 min then final pelleting of band at 214,200×g for 1 h).
  (c) Virus concentrations average ~0.5 mg/mL total viral-protein. Corresponding HA titer, which is a more relevant measure of viral activity, varies among viral species. A "good" preparation of most influenza or hPIV1 is around 64,000 HAU/mL; a "good" preparation of hPIV2 or -3 is around 12,800 HAU/mL.

Reagents:

2. Calcium/magnesium saline for resuspension of virus (after pelleting to removing sucrose or other buffer) and for dialysis: 0.15 M NaCl, 0.25 mM $CaCl_2$, and 0.8 mM $MgCl_2$ (Fisher Scientific).
3. 0.15 M Sodium chloride.
4. 1 M Sodium bicarbonate, pH 9.0.
5. Fluorescent dye with reactive group (for example, Alexa Fluor 488 succinimidyl ester, Molecular Probes).
6. Slide-A-Lyzer Mini Dialysis Units (7,000 MWCO) (Pierce/Thermo Fisher Scientific). 7.9% SDS gel.

II) Assay of Virus Binding to the CFG Glycan Microarray
  1. Glycan microarray-printed slides (CFG).
  2. Cover slips (Fisher scientific).
  3. Humidified Slide processing chambers (Fisher Scientific).
  4. 100-mL Coplin jars for washing slides.
  5. MilliQ water (dH2O).
  6. Cyanine5 (Cy5)-labeled Streptavidin (ZYMED).
  7. TSM buffer: 20 mM Tris-HCl, pH 7.4, 150 mM NaCl, 2 mM $CaCl_2$, and 2 mM $MgCl_2$.
  8. TSM Wash Buffer (TSMW): TSM Buffer+0.05% Tween 20.
  9. TSM-Binding Buffer (TSMBB): TSM buffer+0.05% Tween 20+1% BSA III) Data Analysis of Microarray Binding
  1. Processed glycan microarray slide.
  2. ProScanArray Scanner equipped with multiple lasers for detecting fluorophores (Perkin Elmer).
  3. Image analysis software (Imagene software (BioDiscovery) or Perkin Elmer ScanArray Express).
  4. Data analysis software (Microsoft excel)

IV) Fluorescent Labeling of Virus
  1. To 100 μL of virus in calcium-magnesium saline, add 10 μL of 1 M sodium bicarbonate pH 9.0.
  2. For 100 μL virus (for example, at $1.25 \times 10^4$ HAU/mL), prepare the Alexa Fluor 488 labeling reagent. Typically, ~70 μg of Alexa Fluor 488 succinimidyl ester should be used. This is equivalent to ~0.005 μg dye per HAU (see Note 5).
  3. Resuspend the Alexa Fluor 488 succinimidyl ester in 25 μL dH2O and add to the tube of virus.
  4. Incubate samples for 1 h at room temperature in the dark or wrapped in foil on stirrer, using a 5 mm×2 mm mini Spinbar (Bel-Art Products, 371210010) to stir the sample inside a microcentrifuge tube.
  5. Transfer the entire labeling mixture to a Slide-A-Lyzer Mini Dialysis Unit (7,000 MWCO).
  6. Dialyze against three changes of calcium/magnesium saline at 4° C. (change after 1 h, overnight, then for an additional 1 h). Keep samples in the dark.
  7. Run samples on a 9% SDS gel. Look at the gel under UV light; only the bands corresponding to the known molecular weights of surface proteins should fluoresce. The gel can be subsequently Coomassie stained to confirm band identity if necessary.

V) Assay of Virus Binding to Glycan Microarray
  1. Prepare TSM, TSMW, and TSMBB Buffers (as described above).
  2. Prepare sample(s):
    (a) Prepare 100 μL of virus sample by diluting the fluorescently labeled virus in TSMBB to an appropriate final concentration required for the analysis (e.g. 1:20 dilution of above-prepared virus).
    (b) Prepare 100 μL of Cy5-labeled streptavidin at 0.5 μg/mL final concentration in TSMBB.
  3. Hydrate glycan microarray slides in 100 mL of TSMW in a Coplin Jar for 5 min and drain excess buffer from slide by briefly touching corner of slide to a paper towel.
  4. Lay the slide flat and add 70 μL of the Cy5-streptavidin to the slide.
  5. Slowly place cover slip on the slide, avoiding the formation of bubbles in the sample under the cover slip. If necessary, remove any bubbles by gently tapping the cover slip with a pipette tip or slowly lifting one side of the cover slip. Make sure that the cover slip is properly positioned over the glycan microarray printed in the designated area on the slide.
  6. Incubate slide in a humidified slide-processing chamber in the dark for 1 h at RT or other appropriate time and temperature depending on the experimental design.
  7. When the incubation is complete, remove cover slip by gently allowing it to slip off the slide either directly into the biohazard trash or into a Coplin Jar filled with wash buffer (TSMW).
  8. Wash the slide by gently dipping four times into 100 mL of each of the following buffers in Coplin Jars: (a) TSMW (b) TSM.
  9 Immediately after the TSM wash, drain excess buffer from slide by briefly touching corner of slide to a paper towel and lay the slide flat and add 70 μL of the virus preparation.
  10. Slowly place cover slip on slide, trying to avoid the formation of bubbles in the sample under the cover slip. Remove any bubbles by gently tapping the cover slip with a pipette tip if necessary, or slowly lifting one side of the cover slip. Make sure that the cover slip is properly positioned over the glycan microarray printed in the designated area on the slide.
  11. Incubate slide in a humidified slide-processing chamber in the dark for 1 h at 4° C.
  12. After 1 h incubation, remove cover slip by gently allowing it to slip off into the glass trash/biohazard trash.
  13. Wash the slide by gently dipping four times into 100 mL of each of the following buffers in Coplin Jars: (a) TSMW (b) TSM (c) dH2O.
  14. Spin slide in slide centrifuge for ~15 s or remove dH2O under a gentle stream of nitrogen. Wipe bottom (non-printed) side of the slide with a Kimwipe.

VI) Data Analysis of Microarray Binding
Scanning Slides
  1. Turn on Scan Array Express or other scanner equipped with appropriate lasers for analysis of the selected fluorescent tag(s).
  2. Allow lasers at least 15 min to warm up before scanning.
  3. Configure scanner by selecting the appropriate laser setting for each fluorophore used; i.e. Alexa Fluor 488, Cyanine5 (Cy5), Cyanine3 (Cy3), etc. (a) Check PMT and power of lasers: Standard PMT—(% gain)=70, Laser power=90%.
  4. Select scan protocol that was configured in step 3.
  5. Place slide in scanner with the microarray facing up and the barcode entering the scanner last.

6. Select scan and then Run scan protocol-press OK. Scan takes ~5 min at each excitation wavelength.
7. Each image for each wavelength scanned should be saved separately as a TIF file.

VII) Analyzing Slide Images (Using Imagene Software)
1. Open Imagene software (or another appropriate software if Imagene is not available).
2. Load appropriate TIF image(s).
3. Load appropriate grid file.
4. Load appropriate gene ID file.
5. Align grid. (a) Click Selection: adjust metagrid-click and drag grid to align with biotin spots on the microarray. (b) Click Selection: adjust subgrid-adjust individual grids using biotin spots. (c) Auto adjust spots: click Auto: auto adjust all spots—be sure to be clicked off of any individual grid. (d) Manually adjust spots: click Selection: adjust spots—adjust individual spots so that the entire spot fits inside the circle, and tighten the spots if needed by dragging the lower right corner of the circle to the correct size. If circles are around background spots that have appeared on the slide, the circle can be moved off of the spot.
6. Click Measure: make measurements. This process measures intensity of spots reporting the results as average relative fluorescence units (RFU) of the n=6 spots on the CFG microarray. The results are in the form of a text file, which is used up upload the data onto the CFG website where it is converted to an interactive Bar Chart linked to several databases.
7. Save files.

VIII Analyzing Data
1. The text file is also opened in an Excel macro that is produced for each glycan microarray format. For the CFG glycan microarray, a unique Excel Macro is produced for each version of the glycan microarray.
2. Once the values are calculated, the results of processing by the Excel Macro are presented in an Excel spreadsheet. Here the averages of RFU of binding of virus to individual replicates of the printed glycans are presented in tables, which list the glycan structures with associated RFU values sorted in order of appearance on the microarray in one column and in descending order of Average RFU values in another column. A histogram of RFU plotted vs. glycan number is also generated.
3. Data from glycan microarrays, composed of hundreds of printed glycans, are quite complex. In the case of most influenza or parainfluenza viruses, the data are somewhat simplified because most viruses bind to glycans possessing sialic acid at their non-reducing ends. Thus, for v4.2 of the CFG glycan microarray, there are 123 glycans containing sialic acid in various linkages on a variety of structures that need to be evaluated. Most viruses differentiate between sialic acid-linked α2-3 or α2-6 to a terminal, non-reducing galactose, but may differ—significantly with respect to the underlying glycan structure. Interpretation of the data is currently done by manual inspection of the bound glycan structures. One approach to determine relative binding strengths is by ordering the glycans based on RFU bound. For this data to be valid, one needs to be sure the data are in a linear range. Determining the linear range can be accomplished by doing analyses at multiple concentrations of virus; i.e. from a high dilution to a low dilution using the same slide (to conserve slides) until a constant RFU is obtained for the highest binding glycans. Data from the curve showing about half-maximal binding of the highest binding glycan will be in a linear range. The highest binding glycans under these conditions may be considered the strongest binding glycans. To analyze specificity of binding, it is important to inspect not only what glycans the virus binds, but also what related structures are not bound. We use the following steps for these analyses: (a) The binding assay is carried out at multiple concentrations by preparing a series of two- or fivefold serial dilutions of the stock suspension of labeled virus. Using a single slide, a binding assay is carried out according to the protocols outlined above at the highest dilution of virus. After the slide is analyzed, it is rehydrated in the wash buffer and the next dilution (higher concentration) of virus is applied to the slide. The slide is processed and increasing concentrations are similarly assayed until the RFU of the highest binding glycan(s) stop increasing, which indicates the slide has been saturated. (b) To select the top binding glycans in this analysis, the data at each dilution of virus is normalized by determining the percentile of binding of each glycan relative to the strongest bound glycan. This analysis is performed on two or more assays at non-saturating concentrations of virus to be sure the data are in a linear range. Then the average percentile ranking of each glycan is determined by averaging the Rank of each glycan at each dilution of virus. To order the ranked glycans, the data are sorted according to the Average Rank in decreasing order. This can all be done using an excel Spreadsheet. (c) The analyses were done at dilutions of 1:100, 1:40, 1:20, and 1:10. (d) By calculating the average rank of the binding of each glycan in the linear range (the lower 3 dilutions), an average rank was obtained and the glycans were ordered according to relative binding from highest to lowest ranking. All rankings below 4 percentile were considered weak- or non-binders.
4. The data from the ranked and ordered glycans determined from concentration-dependent binding assays is used to manually determine a motif of binding. (a) Tally up the appearance of particular sugars and linkages in the first, second, third, and/or beyond positions in the binding glycans. (b) Look for the minimum number of sugars in the chains bound. (c) Look for common substituents and the sugars to which they are attached. (d) Look for numbers of branches on the structures. (e) Take all of the above and draw the sequence of the generic bound structure. (f) Take the generic bound structure and look at the nonbinding glycans, especially those that are in the general glycan category. If nonbinding structures that otherwise fit the generic bound motif are found, refine binding motif according to characteristics of these structures.

All references cited herein are incorporated by reference in their entirety.

The invention claimed is:
1. A glycosphingolipid comprising a moiety of formula I:

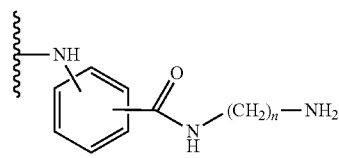

Formula I or salts thereof wherein n is 2, 4, 8 or greater.

2. A purified tagged glycosphingolipid of formula II,

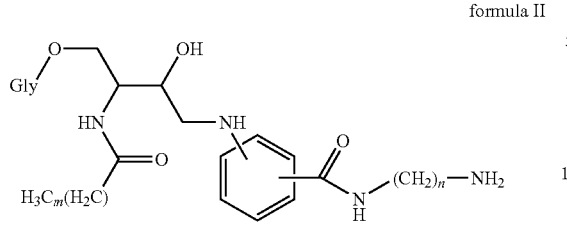

formula II or salts thereof, wherein n is 2, 4, or greater than 4, m is greater than 4, 9, 12, or greater than 13, and Gly is a glycan.

3. A tagged glycosphingolipid conjugated to a solid surface wherein the tagged glycosphingolipid comprises a moiety of formula I:

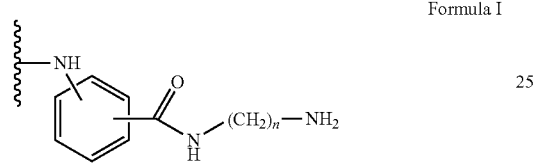

Formula I or salts thereof wherein n is 2, 4, 8 or greater.

4. The solid surface of claim 3, which is a bead, glass slide, polymer, metal, or silicon wafer.

5. The solid surface of claim 3, wherein the tagged glycosphingolipid is conjugated through the sphingolipid.

6. The solid surface of claim 3, wherein the tagged glycosphingolipid is of formula II,

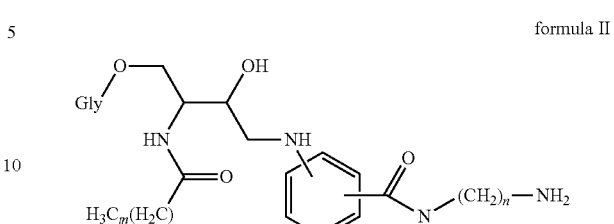

formula II or salts thereof, wherein n is 2, 4, or greater than 4, m is greater than 4, 9, 12, or greater than 13, and Gly is a glycan.

7. A solid surface comprising a plurality of zones wherein the zones comprise purified tagged glycosphingolipids or purified tagged glycans conjugated to the surface provided that at least one of the zones comprises tagged glycosphingolipids and wherein the tagged glycosphingolipid comprises a moiety of formula I:

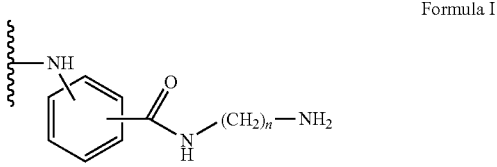

Formula I or salts thereof wherein n is 2, 4, 8 or greater.

* * * * *